United States Patent
Hsieh et al.

(10) Patent No.: US 7,583,780 B2
(45) Date of Patent: Sep. 1, 2009

(54) SYSTEMS AND METHODS FOR IMPROVING A RESOLUTION OF AN IMAGE

(75) Inventors: Jiang Hsieh, Brookfield, WI (US); Jean-Baptiste Thibault, Milwaukee, WI (US); Ken David Sauer, South Bend, IN (US); Charles Addison Bouman, West Lafayette, IN (US)

(73) Assignees: General Electric Company, Schenectady, NY (US); Purdue Research Foundation, West Lafayette, IN (US); The University of Notre Dame du Lac, Notre Dame, IN (US)

( * ) Notice: Subject to any disclaimer, the term of this patent is extended or adjusted under 35 U.S.C. 154(b) by 207 days.

(21) Appl. No.: 11/472,572

(22) Filed: Jun. 22, 2006

(65) Prior Publication Data

US 2007/0297660 A1    Dec. 27, 2007

(51) Int. Cl.
*A61B 6/03* (2006.01)
(52) U.S. Cl. .......................... 378/4; 378/901
(58) Field of Classification Search ............ 378/4, 378/901, 210; 382/131
See application file for complete search history.

(56) References Cited

U.S. PATENT DOCUMENTS

| | | | |
|---|---|---|---|
| 5,404,293 A * | 4/1995 | Weng et al. ............... 378/15 |
| 5,907,594 A * | 5/1999 | Lai ........................... 378/4 |
| 5,909,476 A | 6/1999 | Cheng et al. |
| 6,507,633 B1 * | 1/2003 | Elbakri et al. .............. 378/8 |
| 6,768,782 B1 * | 7/2004 | Hsieh et al. ................ 378/8 |
| 6,907,102 B1 | 6/2005 | Sauer et al. |

OTHER PUBLICATIONS

Hentschel et al., Direct iterative Reconstruction of Computed Tomography Trajectories (DIRECTT), May 9, 2005, Proceedings of the SPIE, vol. 5766, pp. 25-31.*

Fessler, Analytical Approach to Regularization Design for Isotropic Spatial Resolution, 2004, Proc. IEEE Nuc. Sci. Symp. Med. Im. Conf., vol. 3, pp. 2022-2026.*

La Riviere, Reduction of noise-induced streak artifacts in x-ray computed tomography through penalized-likelihood sinogram smoothing. Oct. 2003, IEEE Nuclear Science Symposium Conference Record 2003, vol. 5, pp. 3239-3243.*

Bushberg et al., The Essential Physics of Medical Imaging, 2002, ISBN 0-683-30118-7, pp. 14-15, 263-273, 327-329, 337-348 and 367-369.*

Jaszczak et al., Single Photon Emission Computed Tomography Using Multi-Slice Fan Beam Collimators, 1979, IEEE Trans. Nuc. Sci., vol. NS-26, No. 1, pp. 610-618.*

Hsieh, Computed Tomography: Principles, Design, Artifacts and Recent Advances, 2003, ISBN 0-8194-4425-1, pp. 99-111 and 292-297.*

Dempster et al., Maximum Likelihood from Incomplete Data via the EM Algorithm, 1977, Journal of the Royal Statistical Society B, vol. 1 No. 39, pp. 1-38.*

(Continued)

*Primary Examiner*—Edward J Glick
*Assistant Examiner*—John M Corbett
(74) *Attorney, Agent, or Firm*—Armstrong Teasdale LLP (57) ABSTRACT

A method for reconstructing an image in a tomographic imaging system is described. The method includes improving a spatial resolution of the image by iteratively reconstructing the image.

27 Claims, 6 Drawing Sheets

OTHER PUBLICATIONS

Shepp et al., Maximum Likelihood Reconstruction for Emission Tomography, Oct. 1982, IEEE Transactions on Medical Imaging, vol. MI-1, No. 2, pp. 113-122.*

Lange et al., EM Reconstruction Algorithms for Emission and Transmission Tomography, Apr. 1984, Journal of Computer Assisted Tomography, vol. 8 No. 2, pp. 306-316.*

Hudson et al., Accelerated Image Reconstruction Using Ordered Subsets of Projection Data, Dec. 1994, IEEE Transactions on Medical Imaging, vol. 13 No. 4, pp. 601-609.*

Hebert et al., A Generalized EM Algorithm for 3-D Bayesian Reconstruction from Poisson data Using Gibbs Priors, Jun. 1989, IEEE Transactions on Medical Imaging, vol. 8 No. 2, pp. 194-202.*

Sauer et al., A Local Update Strategy for Iterative Reconstruction from Projections, Feb. 1993, IEEE Transactions on Signal Processing, vol. 41, No. 2, pp. 534-548.*

Bouman et al., A Unified Approach to Statistical Tomography Using Coordinate Descent Optimization, Mar. 1996, IEEE Transactions on Image Processing, vol. 5, No. 3, pp. 480-492.*

Derin et al., Modeling and Segmentation of Noisy and Textured Images Using Gibbs Random Fields, Jan. 1987, IEEE Transactions on Pattern Analysis and Machine Intelligence, vol. PAMI-9, pp. 39-55.*

Bouman et al., Multiple Resolution Segmentation of Textured Images, Feb. 1991, IEEE Transactions on Pattern Analysis and Machine Intelligence, vol. PAMI-13, No. 2, pp. 99-113.*

Villain et al. Three-Dimensional Edge-Preserving Image Enhancement for Computed Tomography, Oct. 2003, IEEE Transactions on Medical Imaging, vol. 22, No. 10, pp. 1275-1287.*

Bouman, et al.; "A Unified Approach to Statistical Tomography Using Coordinate Descent Optimization," IEEE Trans. on Image Processing, Mar. 1996, pp. 1-30, vol. 5, No. 3.

Thibault, et al.; "Three-dimensional Statistical Modeling for Image Quality Improvements in Multi-Slice Helical CT," pp. 1-4.

An International Search Report for corresponding PCT patent application No. PCT/US2007/071917, dated Aug. 14, 2008 (3 pages).

Hentschel et al., "Direct iterative reconstruction of computed tomography trajectories (Directt)", May 9, 2005, Proceedings of the SPIE, vol. 5766, pp. 25-31, Abstract, Sections 1-4 and Figures 1-11 (8 pages).

Fessler, J.A., "Analytical approach to regularization design for isotropic spatial resolution", 2004, Proceedings of the IEEE Nuclear Science Symposium in Medical Imaging Conference, vol. 3, pp. 2022-2026, Abstract, Sections I-IV, Discussion, and Figures 2, 4, and 5 (5 pages).

LaRiviere, P.J., "Reduction in noise-induced streak artifacts in x-ray computed tomography through penalized-liklihood sinogram smoothing", Oct. 2003, IEEE Nuclear Science Symposium Conference Record 2003, vol. 5, pp. 3239-3242, Abstract, Sections II-IV (5 pages).

Bushberg et al., "The Essential Physics of Medical Imaging", 2002, ISBN 0-683-30118-7, pp. 1-15, 263-273, 327-329, 337-348 and 367-369 (36 pages).

Jaszczak et al., "Single Photon Emission Computed Tomography Using Multi-slice Fan Beam Collimators", 1979, IEEE Transactions on Nuclear Science, vol. NS-26, No. 1, pp. 610-618, Abstract and Figure 2 (9 pages).

Hsieh, J., "Computed Tomography: Principles, Designs, Artifacts and Recent Advances", 2003, ISBN 0-8194-4425-1, pp. 99-111 and 292-297 (24 pages).

U.S. Appl. No. 10/991,177, filed Nov. 17, 2004, Sauer et al.

U.S. Appl. No. 10/990,795, filed Nov. 17, 2004, Jean-Baptiste Thibault et al.

Bouman, et al.; "A Unified Approach to Statistical Tomography Using Coordinate Descent Optimization," IEEE Trans. on Image Processing, Mar. 1996, pp. 1-30, vol. 5, No. 3.

Thibault, et al.; "Three-dimensional Statistical Modeling for Image Quality Improvements in Multi-Slice Helical CT," Proceedings of the International Conference on Fully 3D Reconstruction in Radiology and Nuclear Medicine, Salt Lake City, UT, Jul. 6-9, 2005, pp. 271-274.

* cited by examiner

SYSTEMS AND METHODS FOR IMPROVING A RESOLUTION OF AN IMAGE

BACKGROUND OF THE INVENTION

This invention relates generally to imaging systems and more particularly to systems and methods for improving a resolution of an image.

A computed tomography (CT) imaging system typically includes an x-ray source that projects a fan-shaped x-ray beam through a patient to an array of radiation detectors. The beam is collimated to lie within an xy plane, generally referred to as an "imaging plane". Intensity of radiation from the beam received at the detector array is dependent upon attenuation of the beam by the patient. Attenuation measurements from a plurality of detector cells of the detector array are acquired separately to produce a transmission profile.

The x-ray source and the detector array are rotated within a gantry and around the patient to be imaged so that a projection angle at which the beam intersects the patient constantly changes. A group of x-ray attenuation measurements, which is analog projection data, from the detector array at one gantry angle or one projection angle is referred to as a "view". A "scan" of the patient includes a set of views made at varying projection angles, during one revolution of the x-ray source and detector array.

To reduce a total scan time used to acquire multiple slices, a helical scan may be performed. Helical scan techniques allow for large volumes to be scanned at a quicker rate using a single photon source. To perform the helical scan, a table on which the patient rests, is moved along a z-axis about which the gantry rotates while analog projection data for a prescribed number of slices is acquired. The helical scan generates a single helix. The helix mapped out by the beam yields analog projection data from which images in each prescribed slice may be reconstructed. In addition to reducing scan time, the helical scan provides other advantages such as better use of injected contrast, improved image reconstruction at arbitrary locations, and better three-dimensional images. An example of the helical scan includes a multi-slice helical scan. In the multi-slice helical scan, the detector array extends along the z-axis. Typically, in the multi-slice helical scan, the detector array contains multiple rows, with each row corresponding to a different position along the z-axis, and a different measured slice. In an axial scan, analog projection data is processed to construct an image that corresponds to a two-dimensional slice taken through the patient. For discrete slices, iterative reconstruction of a full field of view may be performed to increase image quality.

For continuous scans, a scan pattern in which a position of the patient along the z-axis varies linearly with a rotation of the gantry is produced. During data acquisition, the continuous scan pattern is subject to quantization, and a discrete set of projection views is generated for a limited number of positions of the x-ray source around the patient. Conventional direct image reconstruction techniques, such as two-dimensional or three-dimensional filtered back-projection, reconstruct image voxels from projection data by interpolating elements in the projection data to accumulate contributions from each projection angle into a plurality of image voxels, and thus make an image or an image volume with a single pass over the projection data. A classical resolution of the image generated by applying the filtered back-backprojection is based upon a size of the detector array, a size of a focal spot, a sampling rate of a data acquisition system (DAS) in sampling the analog projection data, and a kernel of a filter that filters the projection data during the filtered back-projection. In a typical scenario, the classical resolution is no finer than the size of a projection of each detector cell at an isocenter of the CT imaging system. By the Nyquist theorem, it is not necessary to sample at more than twice the limiting classical resolution. However, the image volume generated by the conventional direct image reconstruction techniques does not typically have a high spatial resolution.

BRIEF DESCRIPTION OF THE INVENTION

In one aspect, a method for reconstructing an image in a tomographic imaging system is described. The method includes improving a spatial resolution of the image by iteratively reconstructing the image.

In another aspect, an iterative reconstruction method for trading-off a performance of a tomographic imaging system is described. The method includes adjusting a noise and a resolution in a portion of an iteratively reconstructed image.

In yet another aspect, an iterative reconstruction method for adjusting a resolution of a tomographic imaging system is described. The method includes adjusting an in-plane resolution in an iteratively reconstructed image, and adjusting a cross-plane resolution in the iteratively reconstructed image.

In still another aspect, a method for improving a spatial resolution of an image is described. The method includes iteratively reconstructing the image and improving the spatial resolution of the image. The method improves the spatial resolution of the image by at least one of developing a forward projection function having a smooth curve and developing the image having a smooth curve. The development of the forward projection includes developing the forward projection by determining a set of projection values. The development of the image includes reconstructing the image by determining an inverse of the set of projection values.

In another aspect, a processor for improving a spatial resolution of an image is described. The processor is configured to iteratively reconstruct the image and improve the spatial resolution of the image. The processor is configured to improve the spatial resolution of the image by at least one of developing a forward projection function having a smooth curve and developing the image having a smooth curve. The development of the forward projection includes developing the forward projection by determining a set of projection values. The development of the image includes reconstructing the image by determining an inverse of the set of projection values.

DETAILED DESCRIPTION OF THE INVENTION

Iterative reconstruction includes a method that forms an image by repeatedly adjusting an existing estimate according to a quality of a match between actual projection data and expected projection data from a current estimate of the image. The quality of the match may also be affected by consideration of a plurality of characteristics of an image, such as a smoothness of the image and/or satisfaction of a pre-established model. Multiple iterations are performed to create an image that best matches actual projection data based on a pre-defined criterion. A full set of reconstructed images is referred to as a three-dimensional reconstruction, since the set is formed into a three dimensional representation of a patient with each image pixel or picture element corresponding to a single voxel or volume element in the three-dimensional reconstruction.

Figure 1:
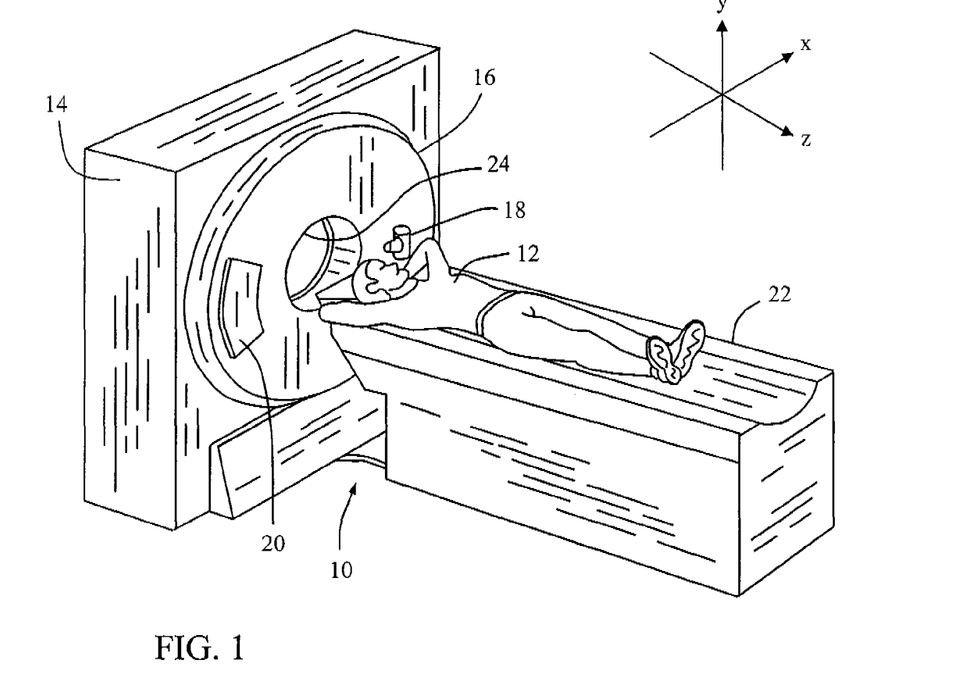
FIG. 1 is an isometric view of an embodiment of a multi-slice CT imaging system implementing a method for improving a resolution of an image.
Figure 2:
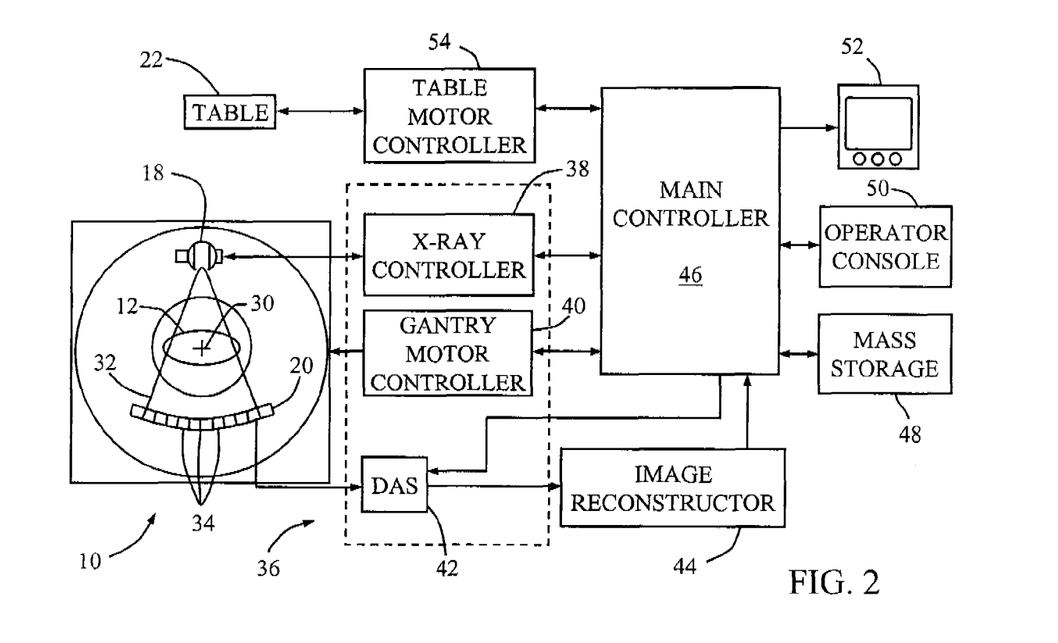
FIG. 2 is a block diagram of the CT imaging system of FIG. 1.

Referring to FIGS. 1 and 2, an embodiment of a multi-slice transmission computed tomography (CT) imaging system 10, utilizing a method of reconstructing an image of an anatomical region of a subject 12, such as a medical patient or a phantom, is shown. CT imaging system 10 includes a gantry 14 that has a rotating inner portion 16 including an x-ray source 18 and a detector array 20. X-ray source 18 and detector array 20 revolve with rotation of gantry 14. X-ray source 18 projects a beam 32 of x-rays toward detector array 20. X-ray source 18 and detector array 20 rotate about subject 12 placed on an operably translatable table 22. Table 22 is translated along a z-axis, parallel to a z-direction, between source 18 and detector array 20 to perform a helical scan of the anatomical region, or stays in the same position along the z axis throughout an axial scan of the anatomical region. Beam 32, after passing through subject 12, within a patient bore 24, is detected at detector array 20 to generate analog projection data that is used to create a CT image of the anatomical region.

X-ray source 18 and detector array 20 rotate about a center axis 30 that is parallel to the z-axis. Beam 32 is received by multiple detector cells 34 in multiple detector rows of detector array 20. Detector array 20 includes multiple rows of detector cells 34 and multiple channels of detector cells 34. The detector channels are parallel to a channel axis, which is parallel to a plane of gantry 24. The detector rows are parallel to a row axis, which is parallel to the z-axis. Each detector row is displaced from all other detector rows in the z-direction along the z-axis about which gantry 24 rotates. Detector cells 34 generate analog projection data, which represent electrical signals corresponding to intensities of beam 32. As beam 32 passes through subject 12, beam 32 is attenuated. Rotation of gantry 14 and an operation of source 18 are governed by a control mechanism 36. Control mechanism 36 includes an x-ray controller 38 that provides power and timing signals to x-ray source 18 and a gantry motor controller 40 that controls a speed or rotation and a position of gantry 14. A data acquisition system (DAS) 42 samples analog projection data from detector cells 34 and converts the analog projection data from an analog form to digital signals to generate sampled and digitized projection data, which is actual projection data. An image reconstructor 44 receives actual projection data from DAS 42 and performs image reconstruction, such as the method for improving a resolution of an image, to generate the CT image. A main controller 46 stores the CT image in a mass storage device 48. Examples of mass storage device 48 include a nonvolatile memory, such as a read only memory (ROM), and a volatile memory, such as a random access memory (RAM). Other examples of mass storage device 48 include a floppy disk, a compact disc—ROM (CD-ROM), a magneto-optical disk (MOD), and a digital versatile disc (DVD).

Main controller 46 also receives commands and scanning parameters from an operator via an operator console 50. A display monitor 52 allows the operator to observe the CT image and other data from main controller 46. Display monitor 52 may be a cathode ray tube (CRT) or alternatively a liquid crystal display (LCD). The operator supplied commands and parameters are used by main controller 46 in operation of DAS 42, x-ray controller 38, and gantry motor controller 40. In addition, main controller 46 operates a table motor controller 54, which translates table 22 to position the anatomical region in gantry 14.

Each of x-ray controller 38, gantry motor controller 40, image reconstructor 44, main controller 46, and table motor controller 54 is not limited to just those integrated circuits referred to in the art as a controller, but broadly refers to a computer, a processor, a microcontroller, a microcomputer, a programmable logic controller, an application specific integrated circuit, and/or any other programmable circuit. X-ray controller 38, gantry motor controller 40, image reconstructor 44, main controller 46, and table motor controller 54 may be a portion of a central control unit or may each be a stand-alone component as shown.

Although the specific embodiment mentioned above refers to a third generation CT imaging system 10, the method for iteratively reconstructing an image equally applies to fourth generation CT systems that have a stationary detector and a rotating x-ray source, to fifth generation CT systems that have a stationary detector and an electron-beam deflected x-ray source, future generations of CT systems involving multiple x-ray sources and/or detectors, and an emission CT system, such as a single photon emission CT system (SPECT) or a positron emission tomographic system (PET).

Additionally, although the methods for iteratively reconstructing an image are described in a medical setting, it is contemplated that a plurality of technical effects of the methods accrue to non-medical imaging systems, such as, those systems typically employed in an industrial setting or a transportation setting, such as, for example, but not limited to, a non-destructive testing system, a baggage scanning system for an airport, other transportation centers, government buildings, and office buildings. The technical effects also accrue to micro PET and CT systems, which are sized to study lab animals as opposed to humans.

Figure 3:
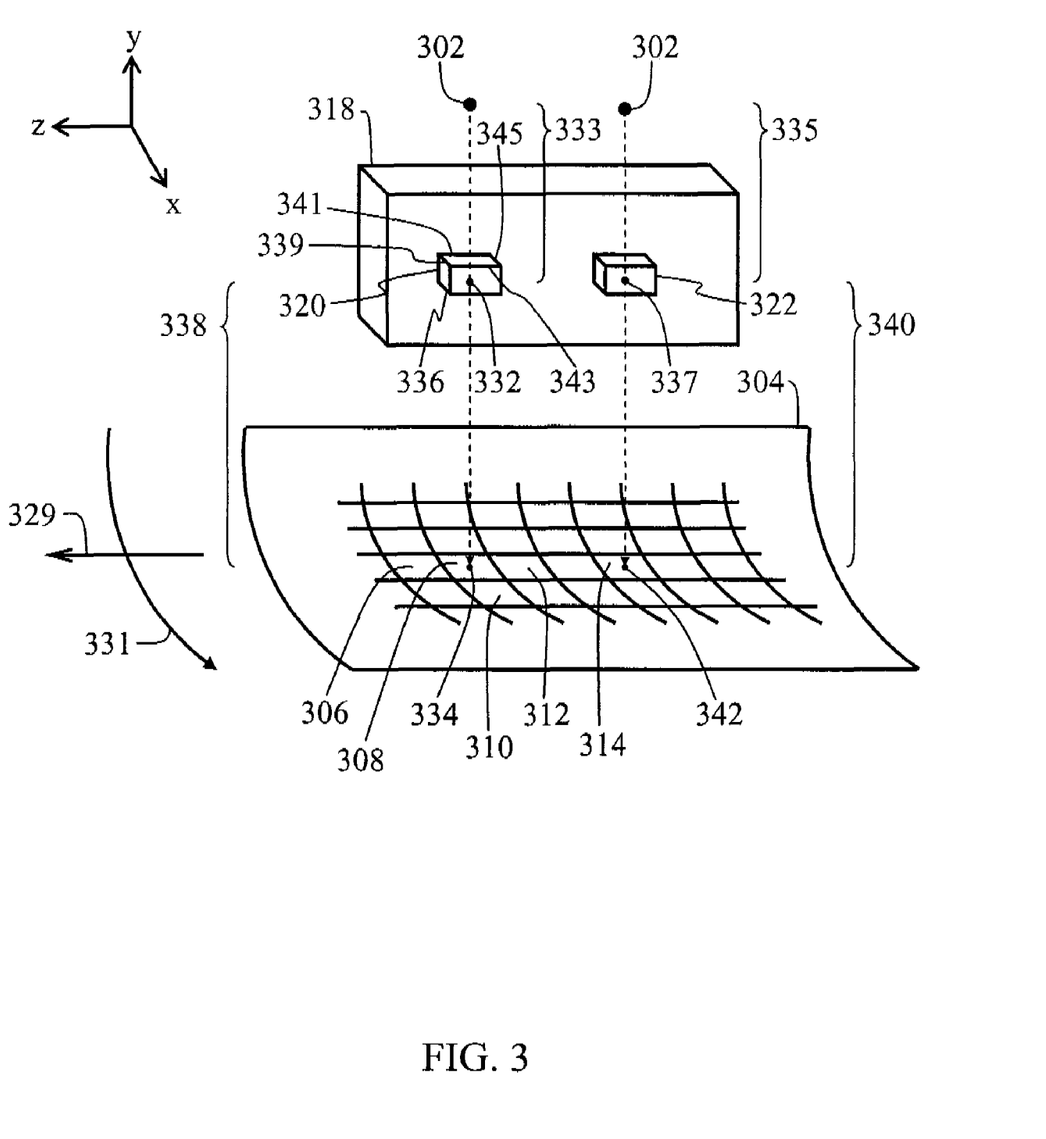
FIG. 3 is a diagram illustrating an embodiment of a method for improving a resolution of an image.
Figure 4:
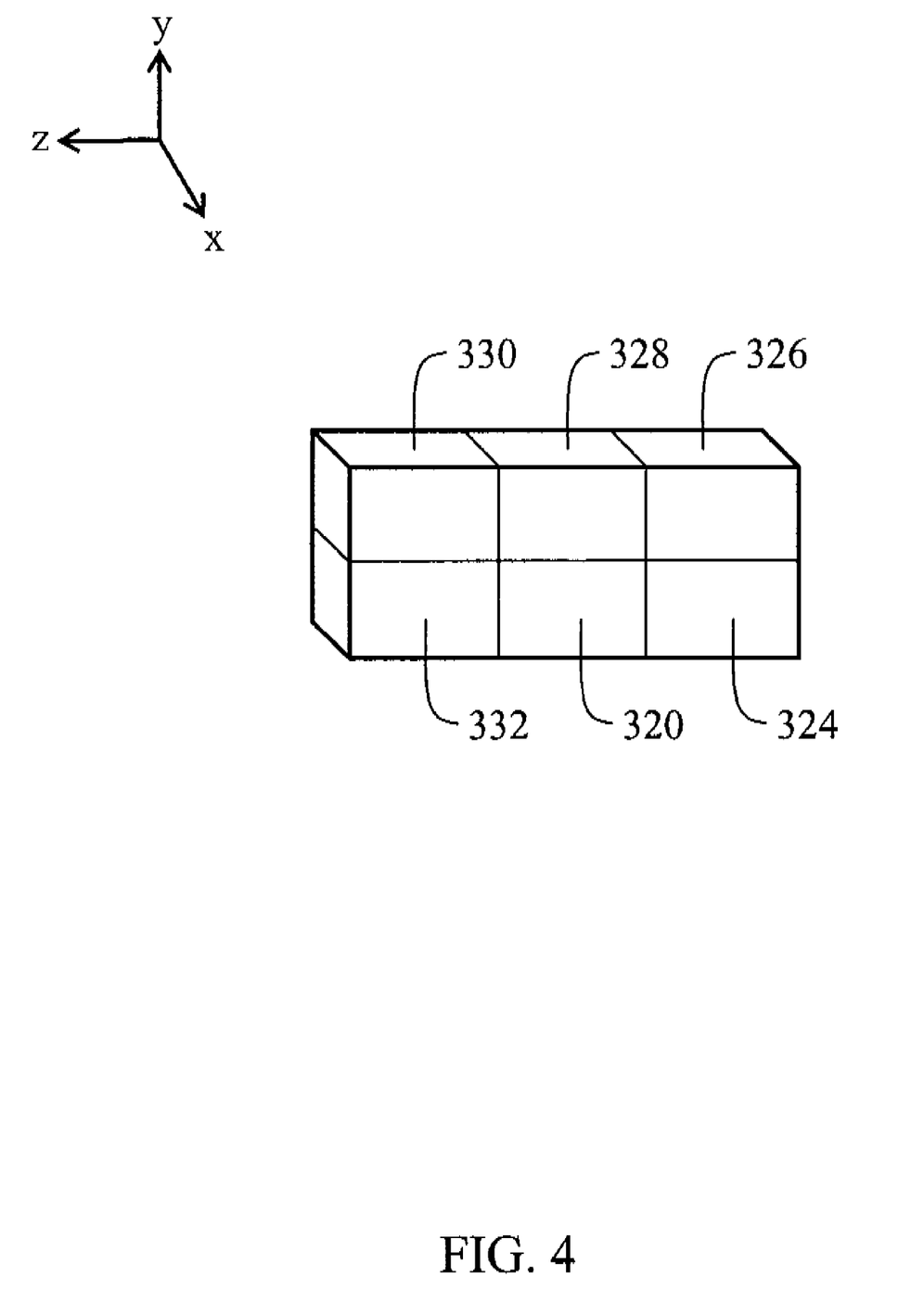
FIG. 4 is a diagram illustrating the method of FIG. 3.
Figure 5:
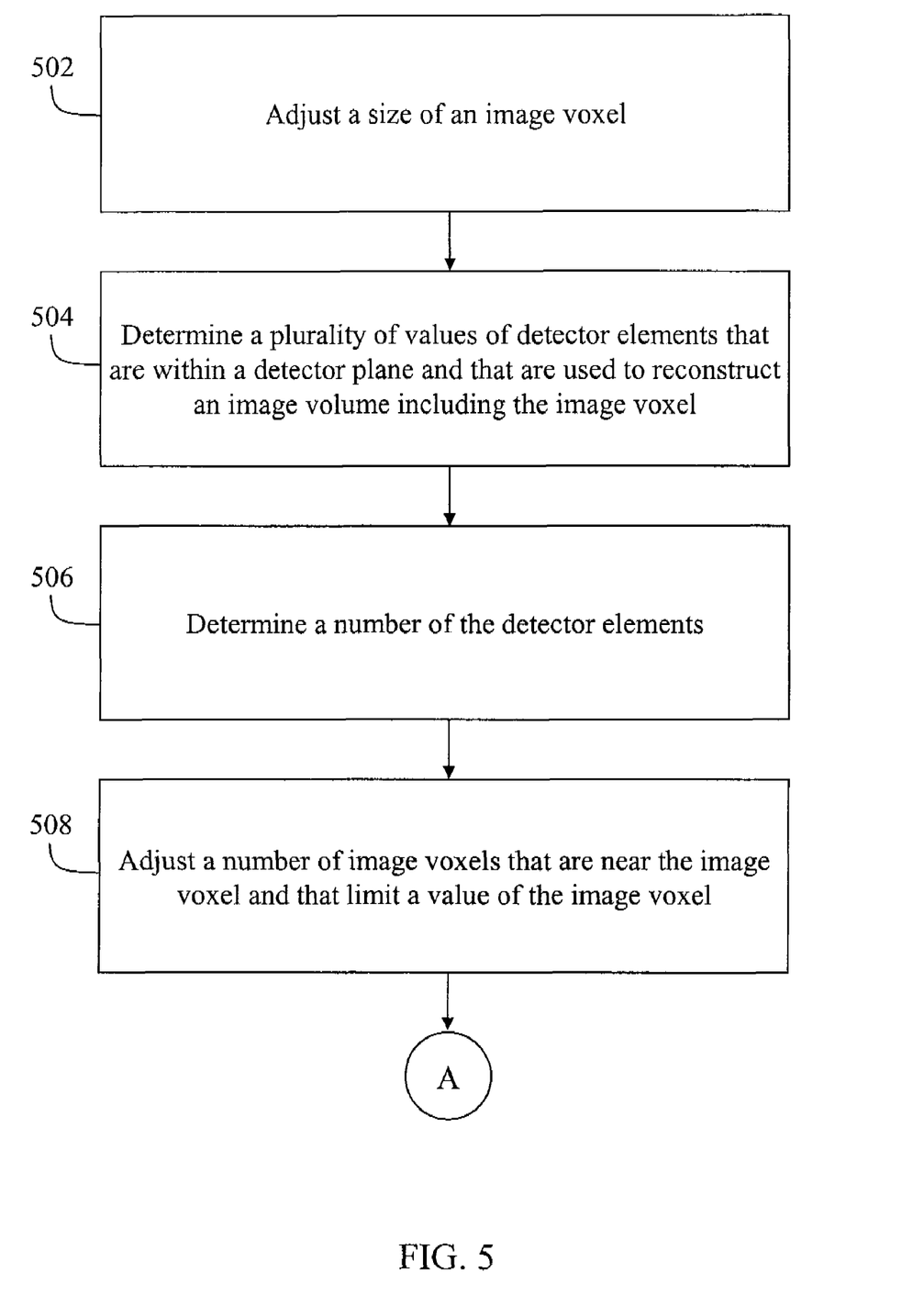
FIG. 5 is a flowchart of an embodiment of a method for improving a resolution of an image.
Figure 6:
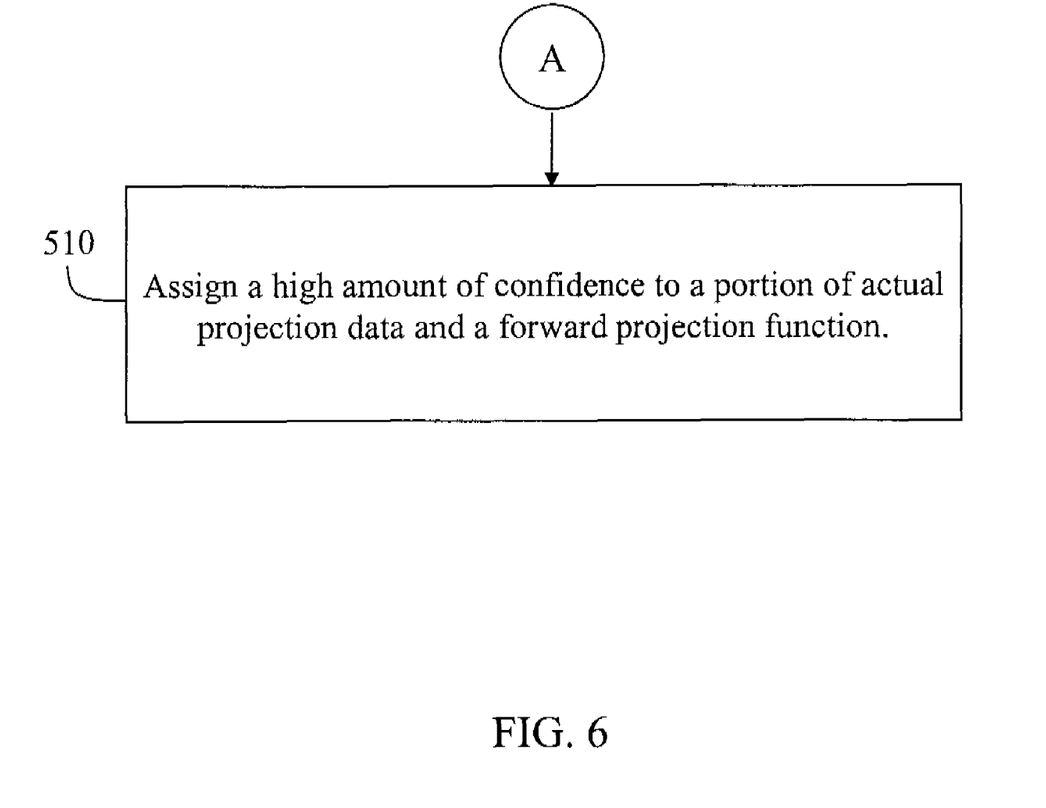
FIG. 6 is a continuation of the flowchart of FIG. 5.

FIGS. 3 and 4 are diagrams and FIGS. 5-6 are flowcharts illustrating an embodiment of the method for iteratively reconstructing an image. A source 302 illustrates a virtual representation of x-ray source 18, a detector plane 304 illustrates a virtual representation of a plane of detector array 20. The plane of detector array 20 faces x-ray source 18. Detector plane 304 includes a plurality of detector elements 306, 308, 310, 312, and 314 and each detector element of detector plane 304 is a virtual representation of detector cell 34. Image reconstructor 44 receives a position of x-ray source 18 from experimental data, such as a change in a shadow of a wire, and generates the virtual representation of x-ray source 18. A change in a location of source 302 is received from the experimental data. As an example, a location of source 302 is determined by placing the wire between x-ray source 18 and detector array 20. The wire is fixed with respect to x-ray source 18 and not fixed with respect to detector array 20. A change in a location of the shadow of the wire formed on detector array 20 provides a change in a location of source 302.

Image reconstructor 44 also receives a position of detector array 20 from a position encoder that detects the position with respect to x-ray source 18. The virtual representations of x-ray source 18 and detector array 20 can be generated by image reconstructor 44 from positions of x-ray source 18 and detector array 20 with reference to an xyz coordinate system illustrated in FIG. 1. A position of source 302 changes to match a change in a position of x-ray source 18 and a position of detector plane 304 changes to match a change in a position of the plane of detector array 20. A distance between source 302 and detector plane 304 is proportional to a distance between x-ray source 18 and the plane of detector array 20.

An optimization problem in the method for iteratively reconstructing an image, for a particular view angle, is expressed as $$\hat{r}(r) = \operatorname*{argmin}_{r}\{D(p - F(r)) + U(r)\} \quad (1)$$

where r represents an image volume 318 that is reconstructed by applying the methods for improving a resolution of an image and that represents the anatomical region of subject 12. Image volume 318 is an example of the image volume r. Image volume 318 includes a value representing an x-ray density, such as a CT number measured in Hounsfield units, of an image voxel 320. Although image voxel 320 is cubical in shape, in an alternative embodiment, an image voxel within image volume 318 is of other shape, such as spherical, elliptical, cylindrical, parallelepiped, trapezoidal, or alternatively, polygonal. In an alternative embodiment, the image volume 318 includes a plurality of values representing x-ray densities of image voxel 320 and of a plurality of image voxels 322, 324, 326, 328, 330, and 332 representing the anatomical region. In an alternative embodiment, image voxel 320 is located parallel to image voxel 322 along one of the x, y, and z-axis. In another alternative embodiment, image voxel 322 may be located at a periphery of image volume 318. In equation (1), p represents actual projection data. In equation (1), F(r) represents a forward projection function or forward projection model of r onto detector plane 304. The forward projection F(r) transforms r in a manner imitative of CT imaging system 10.

In equation (1), U(r) is a regularization function that penalizes local image voxel differences. An example of U(r) includes a convex function, such as a square of a difference between a CT number of image voxel 320 and a CT number of image voxel 328 adjacent to image voxel 320.

Moreover, in equation (1), D is a distortion measure of a mismatch between actual projection data p and the forward projection function F(r) of an estimate of an image. Examples of the distortion measure D include a non-negative convex function, a negative logarithm of a probability density function, and other penalty functions. As another example, the distortion measure D is expressed in a weighted quadratic form in an equation (2) represented as $$\hat{r}(r) = \operatorname*{argmin}_{r}\{(p - F(r))^T W(p - F(r)) + U(r)\} \quad (2)$$

where W is a weighting function and T is a transpose operation. An example of the weighting function includes a diagonal matrix having a plurality of diagonal elements that are inverses of the actual projection data. In an alternative embodiment, any one of equations (1) and (2) does not include U(r). In another alternative embodiment, equation (2) does not include the weighting function W and includes (p−F (r)) instead of W(p−F(r)).

An example of a relationship between r and p includes a linear relationship, such as p=Ar+n, where A is a matrix of values of detector element contributions of detector plane 304, n represents a set of at least one noise value representing a random fluctuation, such as a variance, in p about a mean of actual projection data. During each iteration of equation (1), image reconstructor 44 calculates a perturbation of r which decreases a value of r̂(r) in equation (1) with each iteration. Image reconstructor 44 computes, during a current iteration, the forward projection function F(r) and the regularization function U(r) from a value of r̂(r) calculated during a prior iteration, which is prior to the computation of the forward projection function F(r) and the regularization function U(r). Image reconstructor 44 substitutes, during the current iteration, r̂(r) in place of r in equation (1). During the prior iteration, image reconstructor 44 generates r̂(r) from image volume 318 reconstructed, by filtered back-projection, from actual projection data p. In an alternative embodiment, during the prior iteration, image reconstructor 44 may generate r̂(r) from image volume 318 having a value selected by the operator via operator console 50. A quality of r̂(r) depends strongly on a degree to which the forward projection function F(r) mirrors a physical reality of CT imaging system 10.

Image reconstructor 44 applies the forward projection function F(r) to image voxel 320 to generate a forward projection region including detector element 308 of detector plane 304. As an example, the forward projection region is formed by forward projecting image voxel 320 smaller in size, such as an area, than the classical resolution. In an alternative embodiment, the forward projection region includes more than one detector element, such as, at least two of detector elements 306, 308, 310, and 312. In one embodiment, image reconstructor 44 adjusts 502, such as increases or alternatively decreases, a size of image voxel 320 along at least one of a detector row axis 329 and a detector channel axis 331. Detector row axis 329 is parallel to the z-axis and detector channel axis 331 is parallel to the plane of gantry 14. Detector elements, such as detector elements 308 and 310, are parallel to detector channel axis 331. Detector elements, such as detector elements 306 and 308, are parallel to detector row axis 329. Image reconstructor 44 adjusts a size of image voxel 320 along detector channel axis 331 by adjusting, along at least one of the x-axis and the y-axis, the size of image voxel 320. Image reconstructor 44 adjusts, such as decreases, along at least one of detector row axis 329 and detector channel axis 331, a size of image voxel 320 compared to a size of the forward projection region. For example, image reconstructor 44 decreases a depth of image voxel 320 measured along detector row axis 329 to half a length of the forward projection region measured along detector row axis 329. As another example, image reconstructor 44 decreases a width of image voxel 320 measured along detector channel axis 331 to a third of a width of the forward projection region measured along detector channel axis 331.

Image reconstructor 44 adjusts, during the current iteration, a size of image voxel 320 to improve a spatial resolution, such as at least one of a cross-plane resolution and an in plane resolution, of image voxel 320 compared to a resolution of image voxel 320 during a prior iteration of equation (1) and compared to a convention reconstruction technique, such as filtered back-projection. For example, image reconstructor 44 adjusts a size of image voxel 320 along detector row axis 329 to improve a cross-plane resolution of image voxel 320. As another example, image reconstructor 44 adjusts a size of image voxel 320 along detector channel axis 331 to improve an in-plane resolution of image voxel 320. As yet another example, image reconstructor 44 adjusts a size of image voxel 320 along at least one of detector row axis 329 and detector channel axis 331 so that an in-plane resolution of image voxel 320 is equal to a cross-plane resolution of image voxel 320.

An in-plane resolution is a resolution in a plane along a radial direction in the plane and at an azimuth in the plane. Image reconstructor 44 adjusts a size of image voxel 320 so that all dimensions of image voxel 320 are different from a distance between image voxels 320 and 322.

Image reconstructor 44, in an alternative embodiment, determines or maps a number of detector elements that contribute to a resolution of image voxel 320 by forward projecting, at a projection angle from source 302, image voxel 320 onto detector plane 304. As an example, image reconstructor 44 forward projects a center 332 of image voxel 320 onto detector plane 304 to generate a forward projection point 334 and selects a pre-determined number, such as two or three, of detector elements, within detector plane 304, along at least one of detector row axis 329 and detector channel axis 331. In the example, the pre-determined number is received from the operator via operator console 50. In the example, the detector elements that are selected are adjacent to detector element 308 that includes forward projection point 334. In the example, alternatively, the detector elements that are selected are not adjacent to detector element 308 including forward projection point 334 but are apart from detector element 308 by a number of detector elements of detector plane 304. As another example, image reconstructor 44 forward projects center 332 of image voxel 320 onto detector plane 304 to generate forward projection point 334 and selects a number of detector elements, within the forward projection region, that are located along at least one of detector channel axis 331 and detector row axis 329 and that have a size proportional to a size of image voxel 320. In the example, the size, of detector elements, that is selected by image reconstructor 44 and that is proportional to the size of image voxel 320 includes a depth, along detector row axis 329, of the detector elements. In the example, the depth is twice or alternatively thrice a depth along detector row axis 329 of image voxel 320. A change in a number of detector elements within the forward projection region changes at least one of a size of the forward projection region and a shape of the forward projection region. As yet another example, image reconstructor 44 forward projects image voxel 320 onto detector plane 304 to generate a shadow of image voxel 320 onto detector plane 304 and selects, along at least one of detector row axis 329 and detector channel axis 331, a number of detector elements falling within the shadow of image voxel 320. The shadow of image voxel 320 has the same size, along detector row axis 329 and detector channel axis 331, as that of a bottom surface 336 of image voxel 320. Bottom surface 336 faces detector plane 304. Alternatively, a size of the shadow of image voxel 320 along detector row axis 329 is at least equal to a size of bottom surface 336 along detector row axis 329. In another alternative embodiment, a size of the shadow of image voxel 320 is at least equal to a size of bottom surface 336 along detector channel axis 331. In the example, image reconstructor 44 selects detector elements that are within detector plane 304 and that lie within the shadow of image voxel 320. As still another example, image reconstructor 44 forward projects image voxel 320 onto detector plane 304 by extending a plurality of rays from source 302 via a plurality of edges 339, 341, 343, and 345 of image voxel 320 onto detector plane 304 to generate a forward projection surface on detector plane 304. In the example, image reconstructor selects, along at least one of detector row axis 329 and detector channel axis 331, a number of detector elements lying within the forward projection surface on detector plane 304. As yet another example, image reconstructor 44 forward projects image voxel 320 onto detector plane 304 by extending a plurality of rays from source 302 via a plurality of points on edges 339, 341, 343, and 345 of image voxel 320 onto detector plane 304 to generate a forward projection zone on detector plane 304. In the example, image reconstructor 44 selects, along at least one of detector row axis 329 and detector channel axis 331, a number of detector elements lying within the forward projection zone on detector plane 304. Forward projection point 334 is the center of the forward projection region. In an alternative embodiment, forward projection point 334 is not the center of the forward projection region.

Image reconstructor 44 selects at least one of a number of rows of detector elements along detector row axis 329 and a number of channels of detector elements along detector channel axis 331 by selecting detector elements of detector plane 304. Image reconstructor 44 adjusts a size of detector element 308 to be greater than a size of detector cell 34. For example, image reconstructor 44 increases a volume of detector element 308 to be greater than a volume of detector cell 34. Alternatively, image reconstructor 44 adjusts a size of detector element 308 to be less than a size of detector cell 34. For example, image reconstructor 44 increases a volume of detector element 308 to be less than a volume of detector cell 34. Image reconstructor 44 applies a number of detector elements that are selected and that contribute to a resolution of image voxel 320 to reconstruct r̂(r) in equation (1) and to improve a spatial resolution of r̂(r) compared to the classical resolution generated by the filtered backprojection.

Image reconstructor 44, in another alternative embodiment, determines 504 a plurality of values of detector elements that are within detector plane 304 and that are used to reconstruct image volume 318. For example, image reconstructor 44 randomly assigns a value, such as a positive value or alternatively a negative value, to each detector element within the forward projection region, the forward projection surface, and the forward projection zone of detector plane 304. As another example, image reconstructor 44 assigns a value to each detector element within the forward projection region and to each detector element lying within a forward projection area based on a distance 333 between center 332 of image voxel 320 and source 302 and on a distance 335 between source 302 and a center 337 of image voxel 322. When distance 333 is greater than distance 335, image reconstructor 44 assigns values to a number of detector elements within the forward projection area of image voxel 322 and the number of detector elements is higher than a number of detector elements within the forward projection region of image voxel 320. An assignment of values to the higher number of detector elements within the forward projection area of image voxel 322 results in a resolution of image voxel 322 that is greater than a resolution of image voxel 320. An increase in a resolution of image voxel 322 results in an increase in noise within image voxel 322 and a decrease in the resolution of image voxel 320 results in a decrease in noise within image voxel 320.

Alternatively, when distance 335 is greater than distance 333, image reconstructor 44 assigns values to a number of detector elements within the forward projection region of image voxel 320 and the number of detector elements is higher than a number of detector elements within the forward projection area of image voxel 322. An assignment of values to the higher number of detector elements within the forward projection region of image voxel 320 results in a resolution of image voxel 320 that is greater than a resolution of image voxel 322. An increase in a resolution of image voxel 320 results in an increase in noise within image voxel 320 and a decrease in the resolution of image voxel 322 results in a decrease in noise within image voxel 322.

Image reconstructor 44 forms the forward projection area on detector plane 304 by forward projecting a ray from source 302 via image voxel 322 onto detector plane 304. Image reconstructor 44 iteratively reconstructs image voxel 322 from the forward projection area by applying the systems and methods for improving a resolution of an image. For example, image reconstructor 44 iteratively reconstructs image voxel 322 from the forward projection area upon changing a number of detector elements within the forward projection area to improve a resolution of image voxel 322. The forward projection area is separate from the forward projection region and does not include the forward projection region. Distance 333 between source 302 and center 332 determines a location of image voxel 320 within a field-of-view of x-ray source 18. The field-of-view encompasses image volume 318. Moreover, distance 335 between source 302 and center 337 of image voxel 322 determines a location of image voxel 322 within the field-of-view.

Image reconstructor 44 continues to determine a plurality of values of detector elements that are within detector plane 304 and that are used to reconstruct image volume 318. As an example, image reconstructor 44 determines values of detector elements within the forward projection region by assigning values to the detector elements based on a distance, along at least one of detector row axis 329 and detector channel axis 331, of the detector elements from forward projection point 334. For instance, upon determining, by image reconstructor 44, that a distance, along detector row axis 329, between detector element 306 and forward projection point 334 is greater than a distance, along detector row axis 329, between detector element 308 and forward projection point 334, image reconstructor 44 assigns a lower value to detector element than 306 to detector element 308. As another instance, upon determining, by image reconstructor 44, that a distance, along detector channel axis 331, between detector element 310 and forward projection point 334 is greater than a distance, along detector channel axis 331, between detector element 308 and forward projection point 334, image reconstructor 44 assigns a lower value to detector element 310 than to detector element 308.

Image reconstructor 44 further continues to determine a plurality of values of detector elements that are within detector plane 304 and that are used to reconstruct image volume 318. As an example, image reconstructor 44 assigns a value to each detector element within the forward projection region and to each detector element lying within the forward projection area based on a distance 338 between center 332 of image voxel 320 and forward projection point 334 of the forward projection region and on a distance 340 between center 337 of image voxel 322 and a forward projection point 342 of the forward projection area. When distance 338 is greater than distance 340, image reconstructor 44 assigns higher values to detector elements within the forward projection region than to detector elements within the forward projection area. Alternatively, when distance 340 is greater than distance 338, image reconstructor 44 assigns higher values to detector elements within the forward projection area than to detector elements within forward projection region. Forward projection point 342 is the center of the forward projection area. In an alternative embodiment, forward projection point 342 is not the center of the forward projection area. Distance 338 between center 332 and the forward projection point 334 determines a location of center 332, and distance 340 between center 337 and the forward projection point 342 of the forward projection area determines a location of center 337. As still another example, image reconstructor 44 assigns a plurality of values to detector elements within the forward projection region based on a pre-defined curve. Image reconstructor 44 receives the pre-defined curve from the operator via operator console 50. The pre-defined curve can be a function of at least one of a number of detector elements within the forward projection region, a size, along at least one of detector channel axis 331 and detector row axis 329, of the forward projection region, and a size, along at least one of x, y, and z-dimensions, of image voxel 320. The x-dimension is parallel to an x-axis, the y-dimension is parallel to a y-axis, and the z-dimension is parallel to the z-axis. The y-axis is perpendicular to the z-axis, and the x-axis is perpendicular to both the x-axis and the z-axis. Image reconstructor 44 assigns values of the pre-defined curve to detector elements that are within detector plane 304 and that coincide with the pre-defined curve.

Image reconstructor 44, in an alternative embodiment, assigns values to detector elements within detector plane 304 to satisfy at least one two conditions. A first one of the conditions is that the forward projection function F(r) is a smooth curve that excludes high frequency components, such as impulses. Another example of the high frequency components includes a plurality of rapid local variations that do not correspond to a plurality of slow changes normally expected in the forward projection function F(r). A smooth curve is an example of the pre-defined curve. An example of the forward projection function F(r) is Ar+n. Upon setting, by image reconstructor 44, of r=1 and n=0, image reconstructor 44 determines values of A to generate the forward projection function F(r) as a smooth curve. A second one of the conditions is that image volume 318 is a smooth curve. Upon setting, by image reconstructor 44, n=0, image reconstructor 44 determines values of $A^{-1}$ to generate the image volume 318 as a smooth curve that excludes the high frequency components.

Image reconstructor 44, in another alternative embodiment, determines 506 a number of detector elements within detector plane 304 to achieve a uniform spatial resolution, along at least one of detector channel axis 331 and detector row axis 329, across the field-of-view. For example, image reconstructor 44 determines that a number of detector elements within the forward projection region is equal to the number of detector elements within the forward projection area. As another example, image reconstructor 44 determines that a number of detector elements, along detector row axis 329, within the forward projection region, is equal to a number of detector elements, along detector row axis 329, within the forward projection area. As yet another example, image reconstructor 44 determines that a number of detector elements, along detector channel axis 331, within the forward projection region is equal to a number of detector elements, along detector row axis 329, within the forward projection area. Image reconstructor 44 receives a request for uniform spatial resolution from the operator via operator console 50.

Image reconstructor 44, in yet another alternative embodiment, changes a number of detector elements within the forward projection region based on a trigger frequency of a scan conducted by CT imaging system 10. The trigger frequency determines a discrete number of projection data views collected around subject 12 for a full rotation of the x-ray source 18 around subject 12. As an example, as the trigger frequency to acquire actual projection data used to reconstruct image voxel 320 increases, a number of detector elements selected within the forward projection region decreases. As another example, as the trigger frequency to acquire actual projection data decreases, a number of detector elements selected within the forward projection region increases.

The regularization function U(r) imposes a constraint on image voxel 320 based on values of image voxels near image voxel 320. For example, the regularization function U(r) penalizes a value of image voxel 320 based on a value of at least one of adjacent image voxels 324, 326, 328, 330, and 332. As another example, U(r) penalizes a value of image voxel 320 based on values of image voxels that are not adjacent to image voxel 320 and that lie a number, such as one or two, of image voxels apart from image voxel 320. An example of a penalty on a value of image value based on values of image voxels near image voxel 320 includes that a value of image voxel 320 is not greater than an average of values of the image voxels near image voxel 320. Another example of a penalty on a value of image voxel 320 based on values of image voxels near image voxel 320 includes that a value of image voxel 320 is not greater than a median of values of the image voxels near image voxel 320.

Image reconstructor 44, in still another alternative embodiment, adjusts 508 a number of image voxels, along at least one of detector row axis 329 and detector channel axis 331, that are near image voxel 320 and that penalizes a value of image voxel 320 to improve a spatial resolution of image voxel 320. As an example, image reconstructor 44 adjusts a number of image voxels that are along detector row axis 329 to penalize a value of image voxel 320. As another example, image reconstructor 44 adjusts a number of image voxels that are along detector channel axis 331 to penalize a value of image voxel 320. As yet another example, image reconstructor 44 changes U(r) based on at least one of a function of a position of image voxel 320 within the field-of-view and a size, measured along at least one of the x-axis, y-axis, and z-axis, of image voxel 320. As yet another example, image reconstructor 44 changes U(r) based on a function of a magnitude of a difference between image voxel 320 and at least one of the image voxels near image voxel 320. In an example, U(r)=

$$U(r) = \alpha \sum_C b_{ij}|r_i - r_j|^p \quad (3)$$

where $\alpha$ is a scaling constant, such as a positive real number, p is an exponent parameter, such as a positive real number, and $b_{ij}$ is a directional weighting coefficient, such as a positive real number, $r_i$ represents a value of image voxel 320 at a location i within image volume 318 and $r_j$ represents a value of an image voxel j within image volume 318 near image voxel 320, and C is a neighborhood of the image voxels near image voxel 320 selected to penalize image voxel 320. In the example, image reconstructor 44 changes $\alpha$ and $b_{ij}$ based on a location of image voxel 320 within the field-of-view.

Image reconstructor 44, in one embodiment, adjusts a number of image voxels that are near image voxel 320 and that penalize a value of image voxel 320, and adjusts a number of image voxels that are near image voxel 322 and that penalize a value of image voxel 322, to achieve the uniform spatial resolution, along at least one of a radial direction across the field-of-view, an azimuthal direction across the field-of-view, and a z direction across the field-of-view. For example, image reconstructor 44 determines that a number of image voxels that are near image voxel 320 and that penalize a value of image voxel 320 is equal to a number of image voxels that are near image voxel 322 and that penalize a value of image voxel 322. In an alternative embodiment, image reconstructor 44 adjusts a number of image voxels that are near image voxels 320 and that penalize a value of image voxel 320 and adjusts a number of image voxels that are near image voxel 322 and that penalize a value of image voxel 322 to achieve an isotropic spatial resolution, along at least two of the radial direction, azimuthal direction, and z direction, across the field-of-view. Image reconstructor 44 receives a plurality of values of desired spatial resolutions along at least two of the radial direction across the field-of-view, azimuthal direction across the field-of-view, and z direction across the field-of-view from the operator via operator console 50. In another alternative embodiment, image reconstructor 44 adjusts a number of image voxels that are near image voxel 320 and that penalize a value of image voxel 320 and adjusts a number of image voxels that are near image voxel 322 and that penalize a value of image voxel 322 to achieve a desired spatial resolution, along at least one of the radial direction, azimuthal direction, and z direction, across the field-of-view. Image reconstructor 44 receives the desired spatial resolution from the operator via operator console 50.

Image reconstructor 44 can also change a number of detector elements within the forward projection region and a number of image voxels that are near image voxel 320 and that penalize a value of image voxel 320 to achieve a spatial resolution, such as the uniform spatial resolution, the desired resolution, and the isotropic resolution, along at least one of the radial direction across the field-of-view, azimuthal direction across the field-of-view, and z direction across the field-of-view.

In one embodiment, during a half scan or alternatively a full scan of the anatomical region, image reconstructor 44 assigns 510 a high amount of confidence or weight to a portion of actual projection data and the forward projection function F(r), where the portion and the forward projection function F(r) are generated when source 302 is at a first position and are used to iteratively reconstruct image voxel 320. The high amount of confidence is higher than an amount of confidence that image reconstructor 44 assigns to a portion of actual projection data and the forward projection function F(r), where both the portion and the forward projection function F(r) are generated when source 302 is at a second position and are used to iteratively reconstruct image voxel 320. For example, upon determining that image voxel 320 is iteratively reconstructed from a first set of actual projection data when x-ray source 18 is at a projection angle of zero degrees and is also iteratively reconstructed from a second set of actual projection data when source 302 is at a projection angle of ninety degrees and upon determining that source 302 is closer to image voxel 320 at the projection angle of zero degrees than at the projection angle of ninety degrees, image reconstructor 44 assigns a higher amount of confidence to the first set of actual projection data than to the second portion of actual projection data. The first position is closer to image voxel 320 than the second position. A position of image voxel 320 with respect to source 302 changes with a projection angle of source 302. Image reconstructor 44 changes the distortion measure D that is applied to actual projection data p and to the forward projection function F(r) to change a confidence. For example, image reconstructor 44 increases the distortion measure D from a second power of (p−F(r)) to a third power of (p−F(r)) to increase a confidence.

Image reconstructor 44, in an alternative embodiment, adjusts, such as increases, a number of detector elements within the forward projection region to improve a resolution of image voxel 320 that is deteriorated by a change in a size of a focal spot during acquisition of actual projection data used to iteratively reconstruct image voxel 320. The size of the focal spot includes an area of the x-ray source 18 and beam 32 originates at the area. Further, in another alternative embodiment, image reconstructor 44 shifts a location, along at least one of detector row axis 329 and detector channel axis 331, of forward projection point 334 to improve a resolution of image voxel 320 that is deteriorated by a change in a location of the focal spot during acquisition of actual projection data used to iteratively reconstruct image voxel 320.

Image reconstructor 44, in still another alternative embodiment, shifts a location of forward projection point 334, along the z-axis, to improve a resolution of image voxel 320 that is deteriorated by an error in a measurement of a location, along the z-axis, of table 22 during acquisition of actual projection data used to iteratively reconstruct image voxel 320. Image reconstructor 44, in one embodiment, shifts a location of forward projection point 334 and/or adjusts, such as increases, a number of detector elements, along the z-axis, within the forward projection region to improve a resolution of image voxel 320 deteriorated by a sag of table 22.

Image reconstructor 44, in an alternative embodiment, shifts a location of forward projection point 334, along detector channel axis 331, of the forward projection region with a change in time and/or a change in a projection angle of source 302 to improve a resolution of image voxel 320 deteriorated by vibrations of gantry 14 that occur during acquisition of a portion of actual projection data used to reconstruct image voxel 320. Projection angle of source 302 changes with a change in a location of x-ray source 18. In another alternative embodiment, image reconstructor 44 adjusts at least one of a number of detector elements within the forward projection region and a location of forward projection point 334 of the forward projection region to improve a resolution of image voxel 320 deteriorated by at least one of a change in a size of the focal spot, a change in a location of the focal spot, a change in a location of table 22 along the z-axis, a sag of table 22, and a plurality of vibrations of gantry 14 that occurs during acquisition of actual projection used to reconstruct image voxel 320.

Figure 7:
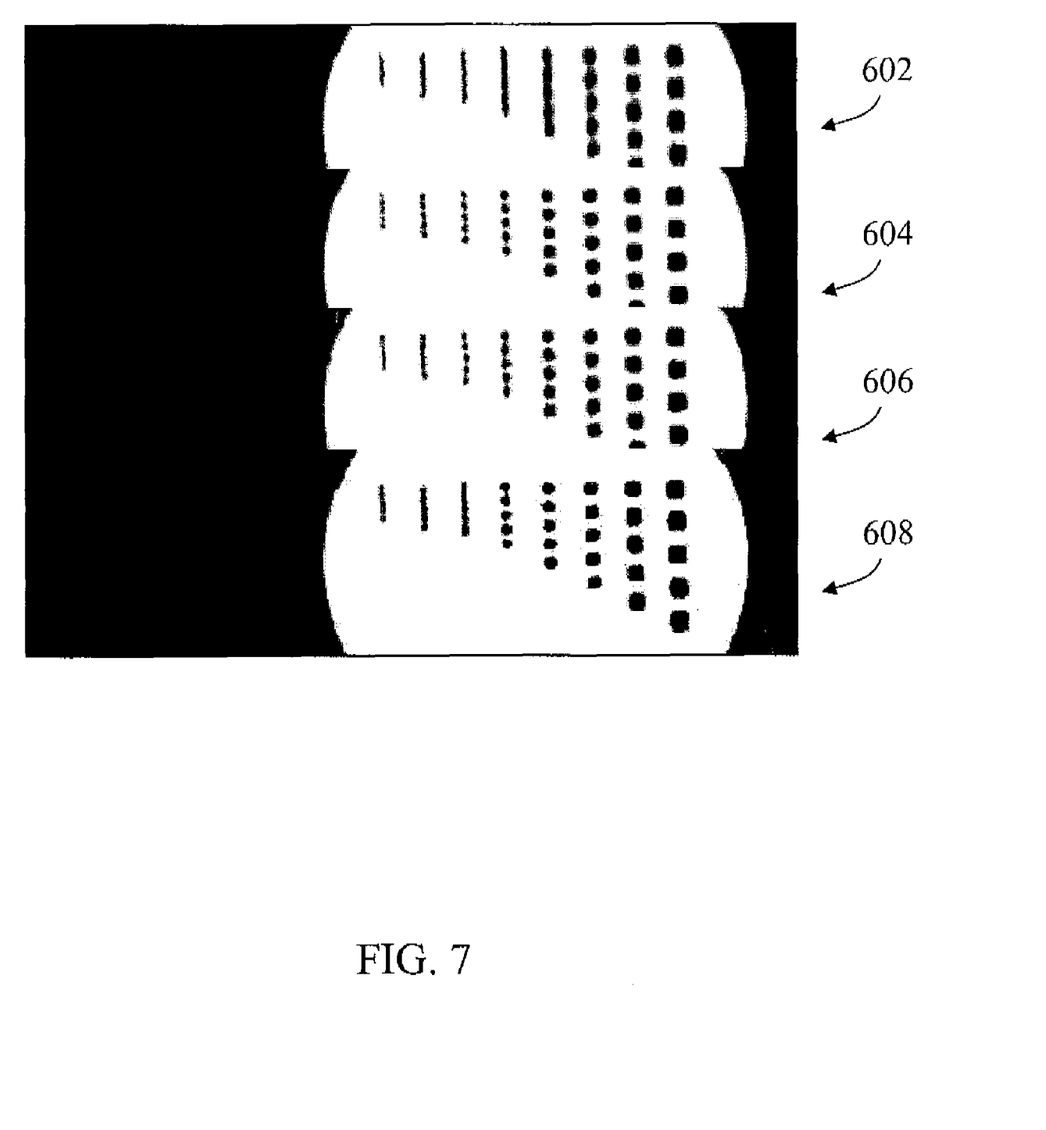
FIG. 7 shows an embodiment of a plurality of images showing an effect of applying an embodiment of a method for improving a resolution of an image.

FIG. 7 shows an embodiment of a plurality of images 602, 604, 606, and 608 created by applying a conventional method and the method for improving a resolution of an image. Images 602 and 608 are reconstructed from the same scan taken at low resolution detector settings. Images 604 and 606 are reconstructed from two separate scans taken at high resolution detector settings. Images 602, 604, and 606 are reconstructed by applying Feldkamp-based reconstruction and image 608 is reconstructed by applying the method for improving a resolution of an image. It is evident that image 608 has better resolution than image 602, and similar resolution compared to images 604 and 606.

Although the systems and methods for improving a resolution of an image are described by using multi-slice CT imaging system 10, the systems and methods are capable of being adapted for various imaging systems including, but not limited to magnetic resonance imaging (MRI) systems, optical scanning systems, CT systems, radiotherapy systems, X-ray imaging systems, ultrasound systems, nuclear imaging systems, magnetic resonance spectroscopy systems, and positron emission tomography (PET) imaging systems. It is also noted that image reconstructor 44 determines a position, with respect to source 302 and detector plane 304, of any of image voxels within image volume 318. It is also noted that in one embodiment, the operator controls image reconstructor 44 via operator console 50 to improve a resolution of an image and decides whether the resolution has been improved.

Technical effects of the systems and methods for iteratively reconstructing an image include improving a resolution of an image. Other technical effects include reducing a variance in a spatial resolution of image voxel 318 by achieving the uniform spatial resolution. An increase in a resolution of an image iteratively reconstructed by applying the system and methods for iteratively reconstructing an image results in a decrease in noise in the image. The variance in a spatial resolution of image volume 318 can be a function of a distance between an isocenter of gantry 14 and any of image voxels 320 and 322. For example, spatial resolution of image voxel 320 decreases with an increase of distance of any of image voxels 320 and 322 from the isocenter. Distance between the isocenter and any of image voxels 320 and 322 changes due to at least one of a shallow angle of beam 32, a finite integration time of DAS 42, heel effects, and other factors. During the finite integration time, DAS 42 integrates a portion of actual projection data acquired at a projection angle. However, in reality, a portion that is within actual projection data and that is integrated is not acquired at an exact projection angle and therefore, an azimuthal blur is created within image volume 318. Image reconstructor 44 reduces the azimuthal blur by selecting a number of detector elements within the forward projection region based on the DAS trigger frequency.

While the invention has been described in terms of various specific embodiments, those skilled in the art will recognize that the invention can be practiced with modification within the spirit and scope of the claims.

What is claimed is:

1. A method for reconstructing an image using a tomographic imaging system, said method comprising:
    generating a first estimate of the image;
    generating a second estimate of the image after generating the first estimate of the image;
    comparing actual projection data and expected projection data of the second estimate of the image;
    adjusting the first estimate using the comparison;
    generating a virtual X-ray source corresponding to a real X-ray source of the tomographic imaging system;
    generating a virtual X-ray detector plane including a plurality of virtual detector elements corresponding to a real X-ray detector array of the tomographic imaging system, the real X-ray detector array including a plurality of detector cells to which the plurality of virtual detector elements correspond;
    determining image volume data that includes a value representing an X-ray density of an image voxel using the virtual X-ray source and the virtual X-ray detector;
    assigning a first weight to a first portion of the actual projection data and a first forward projection function, wherein the first portion of the actual projection data and the first forward projection function are generated when the virtual X-ray source is at a first position and are used to reconstruct the image voxel;
    assigning a second weight to a second portion of the actual projection data and a second forward projection function, wherein the second portion of the actual projection data and the second forward projection function are generated when the virtual X-ray source is at a second position and are used to reconstruct the image voxel, the second weight being lower than the first weight, and the first position being closer to the image voxel than the second position is to the image voxel;
    adjusting the first estimate using the image volume data; and
    outputting the image based on the adjusted first estimate of the image, the output image having a higher resolution than a resolution of the first estimate.

2. A method in accordance with claim 1 further comprising iteratively adjusting the first estimate using a series of subsequent estimates of the image.

3. A method in accordance with claim 2, wherein repeatedly adjusting the first estimate further comprises replacing a prior estimate with a current estimate for determining a subsequent estimate.

4. A method in accordance with claim 1, wherein adjusting the first estimate using the image volume data further comprises adjusting the first estimate using a function of the image volume data, wherein the function uses at least one of actual projection data, a forward projection function, a regularization function, and a distortion measure to adjust the first estimate.

5. A method in accordance with claim 4 wherein using a function of the image volume data further comprises using $\hat{r}(r)=\mathrm{argmin}\{D(p-F(r))+U(r)\}$ as the function, where $\hat{r}(r)$ is the adjusted first estimate, r is the image volume data, D is the distortion measure, p is the actual projection data, F(r) is the forward projection function, and U(r) is the regularization function.

6. A method in accordance with claim 5 further comprising, when a series of estimates are used to adjust the first estimate, replacing r in a current iteration with $\hat{r}(r)$ from a prior iteration to determine a subsequent $\hat{r}(r)$.

7. A method in accordance with claim 4 further comprising using a distortion measure that is a measure of a mismatch between the actual projection data and the forward projection function of the first estimate of the image.

8. A method in accordance with claims 4 further comprising using a distortion measure that is one of a non-negative convex function, a negative logarithm of a probability function, and a weighted quadratic function.

9. A method in accordance with claim 4 further comprising using a regularization function that penalizes a value of the image voxel based on a value of at least one adjacent image voxel.

10. A method in accordance with claim 4 further comprising using a regularization function that penalizes a value of the image voxel based on a value of at least one image voxel that is not adjacent to the image voxel and separate from the image voxel by a predetermined spacing.

11. A method in accordance with claim 4 further comprising adjusting a number of image voxels that are near the image voxel and that penalize a value of the image voxel to at least one of increase a spatial resolution of the image voxel as compared to a first spatial resolution of the image voxel, achieve a uniform spatial resolution across a field of view of the image, achieve an isotropic spatial resolution across the field of view of the image, and achieve a predetermined spatial resolution across the field of view of the image.

12. A method in accordance with claim 1, wherein adjusting the first estimate using the image volume data further comprises applying a forward projection function to the image voxel to generate a forward projection region that includes at least one virtual detector element of the virtual detector plane.

13. A method in accordance with claim 12 wherein applying a forward projection function to the image voxel further comprises adjusting a size of the image voxel relative to the forward projection region along at least one of a virtual detector row of the virtual detector plane and a virtual detector channel of the virtual detector plane.

14. A method in accordance with claim 13 wherein adjusting a size of the image voxel further comprises adjusting the size of the image voxel to increase a spatial resolution of the image voxel as compared to a previous spatial resolution of the image voxel determined during a prior iteration of said adjusting the first estimate.

15. A method in accordance with claim 1, wherein adjusting the first estimate using the image volume data further comprises determining a set of the virtual detector elements that contribute to a resolution of the image voxel by forward projecting the image voxel on to the virtual detector plane at a projection angle from the virtual X-ray source.

16. A method in accordance with claim 15, wherein determining a set of the virtual detector elements further comprises:
    projecting the image voxel on to the virtual detector plane to generate a shadow of the image voxel on the virtual detector plane; and
    selecting a set of the virtual detector elements within the generated shadow as the determined set of the virtual detector elements.

17. A method in accordance with claim 15, wherein determining a set of the virtual detector elements further comprises:
    projecting the image voxel on to the virtual detector plane by extending a plurality of rays from the virtual X-ray source to the virtual detector plane to generate a forward projection surface on the virtual detector plane; and
    selecting the virtual detector elements within the forward projection surface as the determined set of the virtual detector elements.

18. A method in accordance with claim 1, wherein adjusting the first estimate using the image volume data further comprises adjusting a size of one of the virtual detector elements to be one of larger and smaller than a corresponding one of the detector cells of the real X-ray detector array.

19. A method in accordance with claim 1, wherein adjusting the first estimate using the image volume data further comprises determining a plurality of values of a set of the virtual detector elements that are within the virtual detector plane and that are used to reconstruct the image volume data.

20. A method in accordance with claim 19, wherein determining a plurality of values of a set of the virtual detector elements further comprises assigning a value to each of the virtual detector elements that are within a predetermined portion of the virtual detector plane.

21. A method in accordance with claim 19, wherein determining a plurality of values of a set of the virtual detector elements further comprises assigning a value to each of the virtual detector elements based a distance, along one of a virtual detector row axis and a virtual detector channel axis, of each of the virtual detector elements from a predetermined point on the virtual detector plane.

22. A method in accordance with claim 19, wherein determining a plurality of values of a set of the virtual detector elements further comprises assigning a value to each of the virtual detector elements within a predetermine portion of the virtual detector plane based a predetermined curve function.

23. A method in accordance with claim 19, wherein determining a plurality of values of a set of the virtual detector elements further comprises assigning a value to each of the virtual detector elements within the virtual detector plane according to a plurality of predetermined conditions.

24. A method in accordance with claim 1, wherein adjusting the first estimate using the image volume data further comprises determining a number of the virtual detector elements within the virtual detector plane to achieve a uniform spatial resolution across a field of view of the image.

25. A method in accordance with claim 1, wherein assigning the first weight further comprises using a first distortion measure to assign the first weight, and wherein assigning the second weight further comprises using a second distortion measure to assign the second weight, the second distortion measure being different from the first distortion measure.

26. A tomographic imaging system comprising:
an X-ray source configured to generate a beam of radiation;
a detector array configured to receive the beam of radiation; and
an image reconstructor in communication with said X-ray source and said detector array for receiving image data, said image reconstructor configured to:
generate a first estimate of the image;
generate a second estimate of the image after generating the first estimate of the image;
compare actual projection data and expected projection data of the second estimate of the image;
adjust the first estimate using the comparison;
generate a virtual X-ray source corresponding to a real X-ray source of the tomographic imaging system;
generate a virtual X-ray detector plane including a plurality of virtual detector elements corresponding to a real X-ray detector array of the tomographic imaging system, the real X-ray detector array including a plurality of detector cells to which the plurality of virtual detector elements correspond;
determine image volume data that includes a value representing an X-ray density of an image voxel using the virtual X-ray source and the virtual X-ray detector; and
adjust the first estimate by:
applying a forward projection function to the image voxel to generate a forward projection region that includes at least one virtual detector element of the virtual detector plane;
determining a set of the virtual detector elements that contribute to a resolution of the image voxel by forward projecting the image voxel on to the virtual detector plane at a projection angle from the virtual X-ray source;
adjusting a size of one of the virtual detector elements to be one of larger and smaller than a corresponding one of the detector cells of the real X-ray detector array;
determining a plurality of values of a set of the virtual detector elements that are within the virtual detector plane and that are used to reconstruct the image volume data;
assigning a first weight to a first portion of the actual projection data and a first forward projection function, wherein the first portion of the actual projection data and the first forward projection function are generated when the virtual X-ray source is at a first position and are used to reconstruct the image voxel; and
assigning a second weight to a second portion of the actual projection data and a second forward projection function, wherein the second portion of the actual projection data and the second forward projection function are generated when the virtual X-ray source is at a second position and are used to reconstruct the image voxel, the second weight being lower than the first weight, and the first position being closer to the image voxel than the second position is to the image voxel; and
output the image based on the adjusted first estimate of the image, the output image having a higher resolution than a resolution of the first estimate.

27. A method for reconstructing an image using a tomographic imaging system, said method comprising:
generating a first estimate of the image across a field-of-view;
generating a second estimate of the image across the field-of-view after generating the first estimate of the image;
comparing actual projection data and expected projection data of the second estimate of the image;
adjusting the first estimate using the comparison of the second estimate to generate a third estimate of the image across the field-of-view;
generating a fourth estimate of the image across the field-of-view after adjusting the first estimate to generate the third estimate;
comparing the actual projection data and expected projection data of the fourth estimate of the image;
adjusting the third estimate using the comparison of the fourth estimate to generate a fifth estimate of the image across the field-of-view; and
outputting the image based on the fifth estimate of the image, the output image having a higher resolution than a resolution of the first estimate.

* * * * *